US006452059B1

(12) United States Patent
Casagrande et al.

(10) Patent No.: US 6,452,059 B1
(45) Date of Patent: Sep. 17, 2002

(54) CATALYSTS FOR THE OXI-CHLORINATION OF ETHYLENE TO 1,2-DICHLOROETHANE

(75) Inventors: Francesco Casagrande, San Nazzaro Sesia; Marinella Malentacchi, Castiglion Fiorentino, both of (IT)

(73) Assignee: Sud Chemie M.T. S.r.l., Milan (IT)

( * ) Notice: Subject to any disclaimer, the term of this patent is extended or adjusted under 35 U.S.C. 154(b) by 0 days.

(21) Appl. No.: 09/427,360

(22) Filed: Oct. 26, 1999

(30) Foreign Application Priority Data

Nov. 10, 1998 (EP) ............................................ 98830680

(51) Int. Cl.$^7$ ........................ C07C 17/156; B01J 23/04; B01J 23/02; B01J 23/72
(52) U.S. Cl. ........................ 570/245; 570/243; 502/344; 502/345
(58) Field of Search ................................ 502/243, 244, 502/344, 345; 570/243, 245

(56) References Cited

U.S. PATENT DOCUMENTS

| 4,323,716 A | * | 4/1982 | Canavesi et al. ............ 570/243 |
| 4,377,491 A | * | 3/1983 | Canavesi et al. ............ 252/441 |
| 4,414,136 A | * | 11/1983 | Convers ...................... 502/225 |
| 4,460,699 A | * | 7/1984 | Convers et al. ............... 502/84 |
| 4,740,644 A | | 4/1988 | Eichhorn et al. |
| 4,814,113 A | * | 3/1989 | Cuzzato et al. .......... 260/544 F |
| 5,053,567 A | | 10/1991 | Correia et al. |
| 5,154,911 A | * | 10/1992 | Benson et al. ............... 423/502 |
| 5,387,708 A | * | 2/1995 | Molzahn et al. ............. 502/164 |
| 5,569,798 A | * | 10/1996 | Jackson ....................... 570/178 |
| 5,639,436 A | | 6/1997 | Benson et al. ............... 423/502 |
| 5,854,168 A | * | 12/1998 | Stauffer ...................... 502/225 |
| 5,861,353 A | * | 1/1999 | Viola et al. .................. 502/225 |
| 6,008,399 A | * | 12/1999 | Chang et al. ................ 558/277 |

FOREIGN PATENT DOCUMENTS

DE     B - 23 56 549     3/1975

* cited by examiner

Primary Examiner—Stanley S. Silverman
Assistant Examiner—Christina Ildebrando
(74) Attorney, Agent, or Firm—Welsh & Katz, Ltd.

(57) ABSTRACT

A catalyst for the oxi-chlorination of ethylene to 1,2-dichloroethane which comprises cupric oxychloride (CuOHCl) as an active component. CuOHCl is preferably supported on a porous support such as alumina and used in fixed-bed oxi-chlorination processes.

12 Claims, No Drawings

CATALYSTS FOR THE OXI-CHLORINATION OF ETHYLENE TO 1,2-DICHLOROETHANE

The present invention relates to catalysts for the oxi-chlorination of ethylene to 1,2-dichloroethane.

BACKGROUND OF THE INVENTION

The catalyst that is generally used for oxi-chlorination of ethylene to 1,2-dichloroethane is constituted by cupric chloride supported on an inert porous oxide carrier such as alumina.

The catalyst is preferably used on a fixed bed.

In order to inhibit the reactions that lead to formation of byproducts such as ethyl chloride and carbon oxides, the cupric chloride is used in a mixture with promoters such as potassium chloride.

Mixtures of potassium chloride with cesium chloride have also been used in order to inhibit the formation of byproducts without having a negative effect on the catalytic activity (EP-A-62 320).

Known from DE 23 56 549 is a process for preparing 1,2-dichloroethane by oxi-chlorination of ethylene using a catalyst system obtained by impregnation of a carrier with an aqueous solution of $CuCl_2 \cdot 3Cu(OH)_2$ and HCl, followed by heating, thereby $CuCl_2$ is formed.

DESCRIPTION OF THE INVENTION

It has now been found unexpectedly that cupric oxychloride, Cu(OH)Cl, is a highly effective catalyst for the oxi-chlorination of ethylene to 1,2-dichloroethane, which provides a higher performance, in terms of selectivity and conversion, than cupric chloride or other copper compounds, such as cuprous chloride (CuCl) or cupric hydroxychloride of formula $Cu_2(OH)_3Cl$. The selectivity of the catalyst remains high even when working with high conversions.

The addition of promoters such as potassium chloride further improves the selectivity without reducing catalytic activity.

Potassium chloride can be used in a mixture with magnesium chloride and/or cesium chloride or other chlorides of the rare earths; it is used with a ratio of K/Cu to cupric oxychloride of 0.05:1 to 1.2:1.

Cupric oxychloride is prepared by oxidizing $CuCl_2$ with air in the presence of moisture, working at room temperature or slightly above. In practice, the cupric chloride is left in contact with the humid air until conversion to Cu(OH)Cl occurs.

For use on a fixed bed, the cupric oxychloride is supported on porous inert oxides such as alumina.

Alumina is preferably used, or even more preferably mixtures of alumina with silica, containing more than 80% alumina by weight, are used.

It has in fact been found, and this constitutes another aspect of the invention, that the use of supports prepared from mixtures of boehmite with aluminum silicate allows to considerably improve the catalytic activity without reducing the selectivity of the catalyst.

The weight ratio between boehmite and aluminum silicate is preferably between 60:40 and 90:10.

The alumina that can be used as support generally has a surface area (BET) of more than 200 $m^2/g$, preferably between 240 and 300 $m^2/g$, and a porosity of 0.5–0.65 $cm^3/g$; the volume of the pores with a radius of less than 50 A is 0.4–0.55 $cm^3/g$.

Alumina/silica mixtures obtained from boehmite and from aluminum silicate have a surface area greater than alumina.

In the case of the support obtained from boehmite and from aluminum silicate in an 80:20 mixture by weight, the area is approximately 290 $m^2/g$ and porosity is 0.6 $cm^3/g$.

The supported catalysts have surface area generally comprised from 130 to 200 $m^2/g$.

Impregnation of the cupric oxychloride on the porous support is performed by using aqueous solutions of the oxychloride in an amount which is smaller than the volume of the pores of the substrate, for example equal to 90% of the volume.

The amount of oxychloride fixed on the substrate, expressed as copper, is comprised from 1 to 10% by weight, preferably 5–6%.

The support is in the form of granules whose geometric shape ranges from spherical to solid cylindrical to cylindrical with a through bore or bores to lobate cylindrical with through bores at the lobes.

Preferably, lobate cylindrical shapes with three or more lobes, with through bores having an axis which is substantially parallel to the axis of the granule and substantially equidistant and parallel with respect to each other, are used.

Granules having a three-lobed cross-section with through bores at the three lobes are preferred. The ratio between the surface and the volume of granules of this type of support is at least 2.4 $cm^{-1}$.

The height of the granules is comprised from 3 to 10 mm, preferably 4–7 mm.

The radius of the circumscribed circumference is from 2 to 5 mm.

Cylindrical granules with three or more lobes provided with through bores are described in EP-B-591 572, the description of which is included herein by reference.

The lobate and perforated granules are preferably prepared by compression tableting, using lubricant applied to the surface of the mold and punches.

Solid lubricants, such as magnesium stearate and stearic acid, are preferably used.

The use of catalysts in the form of cylindrical granules having lobes and through bores allows to significantly reduce pressure load losses and to improve the catalytic activity and selectivity.

By using the catalysts in their lobate and perforated forms, it is also possible to conduct the oxi-chlorination reaction in a single stage instead of three, as normally occurs when using catalysts having a solid cylindrical shape.

For single-stage operation, a large excess of ethylene with respect to the hydrochloric acid is used. This allows to improve the reaction selectivity by virtue of the high specific heat of ethylene.

The reactor that can be used is generally of the tubular type formed by a bundle of tubes which have a diameter between 20 and 40 mm and are connected to each other and to a cooling jacket.

The gaseous mixture comprising ethylene, hydrochloric acid and air or oxygen is fed from below toward the top of the reactor.

The temperature of the reaction is generally between 210° and 350° C., with residence times between 1 and 6 seconds.

The loading of the catalyst in the reactor, in the case of the single-stage process, is performed in a plurality of layers, with a catalytic mass concentration profile which increases from the bottom upwards.

In the case of the three-stage process, the reactor of the third stage works with the highest concentration of catalyst.

The following examples are given to illustrate but not to limit the invention.

EXAMPLES

Preparation of the Support

A commercial boehmite (specific surface=331 $m^2/g$; pore volume=1.59 $cm^3/g$) mixed with stearic acid is granulated in order to obtain a powder with a particle size between 100 and 600 microns.

The powder is compression tableted so as to obtain cylindrical granules with three lobes and three through bores, measuring 5×5 mm.

The granules are then calcined in an air stream at 450° C. for 4 hours.

Supports have been prepared by mixing the boehmite with a commercial silica-alumina (containing 30% $SiO_2$ by weight) with an 80:20 weight ratio. The silica-alumina used has a specific surface of approximately 470 $m^2/g$ and pore volume of 1.37 $cm^3/g$.

The final silica concentration in the tableted and calcined support is approximately 7% by weight.

Preparation of the Catalyst

The impregnating solutions that contain the copper salt and the promoter (KCl) are prepared so as to obtain on the finished catalyst final Cu concentrations between 5 and 6% and promoter concentrations of 0.5–2% expressed as K. The volume of the aqueous solution used for impregnation is equal to approximately 90% of the total volume of the pores of the support. Total dissolution of the salts is achieved by adding HCl in a variable amount (1–30 g HCl/100 g of solution) according to the solubility of the copper salt used.

The solution is sprayed by means of an atomizer of the Venturi type onto the support contained in a jar which is turned at a rate which allows optimum gradual full exposure of the surface of the support.

The catalyst is then dried at 150° C. for 12 hours.

Oxi-chlorination Reaction

In order to determine the activity of the catalyst, a tubular reactor made of nickel, with an internal diameter of 26.6 mm and a height of 1,300 mm, installed in a temperature-control bath of silicone oil, was used. The catalyst was loaded by using the. following bottom-up loading profile:

a first layer, 250 mm thick, formed by graphite;

a second layer, 800 mm thick, formed by the catalyst alone.

A gaseous stream of the reagents is made to pass through the reactor from the bottom upwards with the following flow-rates for the components:

ethylene: 232 Nl/h

HCl: 71 Nl/h $O_2$: 19 Nl/h $N_2$: 422 Nl/h

The temperature of the temperature-control bath is 210° C.; the supply pressure is 1.5 atmospheres and the contact time is 1.6 seconds.

Example 1

The catalyst is prepared starting from cupric oxychloride. Potassium chloride is used as promoter. The support is constituted by alumina. The characteristics of the catalyst and the data on its activity are listed in table 1.

Comparison examples 1–3

The catalysts used in these examples are prepared starting from cuprous chloride, cupric hydroxychloride ($CU_2(OH)_3Cl$) and cupric chloride.

Potassium chloride is used as promoter; the support is constituted by alumina.

Examples 2–3

TABLE

| EXAMPLE | Cu SALT | SPECIFIC AREA $m^2/g$ | Pore volume $cm^3/g$ | HCL conversion % | EDC sel. % | $CO_x$ sel. % | EC sel. % | EDC purity % | Hot spot ° C. |
|---|---|---|---|---|---|---|---|---|---|
| 1 | Cu(OH)Cl | 180 | 0.42 | 94.96 | 98.65 | 1 | 0.05 | 99.7 | 273 |
| comp. 1 | CuCl | 139 | 0.43 | 92.90 | 98.78 | 0.8 | 0.12 | 99.7 | 267 |
| comp. 2 | Cu2(OH)$_3$Cl | 169 | 0.39 | 93.58 | 98.65 | 1 | 0.05 | 99.7 | 265 |
| comp. 3 | $CuCl_2$ | 145 | 0.35 | 93.52 | 98.39 | 1.27 | 0.04 | 99.7 | 272 |

Catalysts contain 5–6% Cu and 0.8% K (% by weight)
EC - ethyl chloride
EDC - 1,2-dichloroethane
Hot spot - maximum temperature measured inside the reactor.

The disclosures in European Patent Application No. 98830680.9 from which this application claims priority are incorporated herein by reference.

What is claimed is:

1. A catalyst for the oxi-chlorination of ethylene to 1,2-dichloroethane, comprising cupric oxychloride of the formula Cu(OH)Cl as an active component, and a promoting component selected from the group consisting of potassium chloride and magnesium chloride, said components being supported on an inert porous oxide.

2. The catalyst according to claim 1, wherein the inert support comprises alumina or alumina-silica mixtures containing more than 80% alumina by weight.

3. The catalyst according to claim 2, wherein the alumina-silica mixtures are obtained from boehmite mixed with aluminum silicate, and having a surface area of more than 200 m$^2$/g.

4. The catalyst according to claim 2, having a surface area of from 130 to 200 m$^2$/g.

5. The catalyst according to claim 1, wherein the cupric oxychloride is supported in an amount between 1 and 10% by weight, expressed as copper.

6. The catalyst according to claim 1, wherein the the promoting component is potassium chloride, optionally comprising magnesium chloride and/or cesium chloride.

7. The catalyst according to claim 6, wherein the ratio of potassium chloride to cupric oxychloride, expressed as K/Cu, is in the range of 0.05:1 to 1.2:1.

8. The catalyst according to claim 1, wherein the components are supported on lobate cylindrical granules provided with through bores in the lobes which are substantially parallel to the axis of the cylinder.

9. The catalyst according to claim 8, wherein the cylindrical granule has three lobes and a height of from 3 to 10 mm.

10. The catalyst according to claim 9, wherein the granule has an area to volume ratio greater than 2.4 cm$^{-1}$.

11. A method for the oxi-chlorination of ethylene to 1,2-dichloroethane comprising contacting ethylene with oxygen, or a gas containing oxygen, and hydrochloric acid, wherein the oxi-chlorination reaction is performed in a fixed-bed reactor loaded with granules of a catalyst according to claim 1.

12. The method according to claim 11, wherein the oxi-chlorination reaction is performed in a single stage, using an excess of ethylene with respect to the stoichiometric quantity of hydrochloric acid.

* * * * *